United States Patent [19]

Berndt

[11] Patent Number: 5,580,784

[45] Date of Patent: Dec. 3, 1996

[54] DATA COLLECTION APPARATUS FOR USE WITH CHEMICAL SENSORS

[75] Inventor: Klaus W. Berndt, Stewartstown, Pa.

[73] Assignee: Becton Dickinson and Company, Franklin Lakes, N.J.

[21] Appl. No.: 129,239

[22] Filed: Sep. 29, 1993

[51] Int. Cl.$^6$ .................................. C12M 1/34; C12Q 1/04
[52] U.S. Cl. .................................. 435/288.7; 435/288.1; 435/34; 436/164; 356/349; 250/461.2; 422/82.01; 422/82.05
[58] Field of Search .................... 382/66; 250/461; 436/807, 809, 172, 164; 435/968, 20, 34, 288.7, 288.1; 356/349, 51, 319; 422/82.05, 82.01

[56] References Cited

U.S. PATENT DOCUMENTS

| | | | |
|---|---|---|---|
| 3,787,124 | 1/1974 | Lowy et al. | 356/205 |
| 5,164,301 | 11/1992 | Thompson et al. | 436/172 |
| 5,186,536 | 2/1993 | Bornhorst et al. | 362/293 |
| 5,397,709 | 3/1995 | Berndt | 436/34 |
| 5,422,720 | 6/1995 | Berndt | 356/343 |
| 5,473,437 | 12/1995 | Blumenfeld et al. | 356/417 |

Primary Examiner—Esther M. Kepplinger
Assistant Examiner—Milton I. Cano
Attorney, Agent, or Firm—Alan W. Fiedler

[57] ABSTRACT

An apparatus utilizing chemical sensors to determine whether a particular sample vial is evidencing bacterial growth includes directing radiation sources having closely spaced wavelengths into the sample vial. Emissions from the chemical sensor due to the two spectrally spaced radiation sources are monitored, and a ratio of their differences and sums is calculated. The inventive ratio eliminates station-to-station variation between the radiation sources or detectors, and also any lot-to-lot variations in the sensor materials. An absolute indication of the conditions within the sample vial may thus be taken eliminating the prior art, station-to-station variations and lot-to-lot variations in the sensors resulted in varying readings for positive and negative samples. Thus, any one reading could not be utilized to make a prediction of whether a particular sample is a positive or a negative. With the inventive apparatus, each absolute readings can be utilized to provide an indication of whether a particular sample is positive or negative at any time.

8 Claims, 7 Drawing Sheets

DATA COLLECTION APPARATUS FOR USE WITH CHEMICAL SENSORS

BACKGROUND OF THE INVENTION

This application in general relates to a method for collecting data from a chemical sensor. The inventive method eliminates variations in monitored readings from the chemical sensors which may result based on variations in the composition of the chemical sensors, or based on station-to-station variations between several of the sensors and their associated monitoring devices.

Known chemical sensors are utilized in combination with a blood culture vial to monitor changes in the blood culture vial. As is known, a small quantity of blood is injected into a vial which contains a culture medium. A chemical sensor is positioned inside the vial. The vial is then incubated and monitored for bacterial growth.

Known chemical sensors include a variety of types of sensors which change their light absorption or fluorescent intensity based on changes within the culture medium. Radiation is directed into the chemical sensor, and the intensity of a resultant emission is monitored. The blood culture medium is tested by monitoring the emission over time to detect changes in emission intensity from the chemical sensor. If the blood sample is a "positive" and contains bacteria, then it is expected that the emission would change with time. In known systems, the emissions are monitored over a period of days to determine whether there is a change. The monitored emissions may be relatively static for a period of days, but may then change drastically to evidence the presence of bacteria in the sample. Such known systems have been widely utilized and have experienced great success.

Some deficiencies remain with these systems, however, since the testing systems for use with the chemical sensors are typically testing hundreds of sample vials at any given time. The monitored emission from any particular chemical sensor can vary with variations between the light source positioned adjacent to the sensor, the chemical sensor itself, and with a light detector positioned adjacent to the chemical sensor. Thus, an absolute determination of whether a particular vial is positive or negative upon any one given reading has not been possible with the prior art systems. Rather, the emission at any one point in time provides little information with regard to the status of the sample vial. The emissions must be monitored over a period of time to detect the changes in the emissions which indicate a positive sample.

Problems arise with sample vials which have been prepared from a relatively long period of time relative to the typical sample vial. As an example, a sample vial may be prepared on a Friday and tested on a Monday. In such so-called "late" sample vials, it is possible that the sample vial has already turned positive, that all changes have occurred, and that monitoring to detect changes in the emissions will be of no avail. There may be no further changes, and thus the monitoring will detect no changes which would give rise to an indication that the sample vial is positive.

Further, with the variation that is inherent in the prior art sensor readings, it is possible that a positive readings for a sample from a first sensor at a first station might be of values that are roughly equivalent to negative readings for other samples at other stations. For that reason, no reliance can be made on the absolute value of any reading. Given that fact, the above-described problem of a late vial could result in the failure to ever detect the late vial as being a positive.

It has been proposed to address the problem of station-to-station or sensor-to-sensor variations by taking two readings from each sensor based upon two distinct wavelength radiations being directed into the sensor. Such prior art systems have hoped to eliminate station-to-station or sensor-to-sensor variation by taking a ratio of those two readings. However, it has been found that variables within the station and within the sensor vary with varying wavelengths. Thus, the prior art use of a ratio based on two wavelengths has not fully addressed the above-discussed problems. The variation with the changing wavelengths is smallest when the change in wavelengths is kept to a minimum. However, when a small wavelength change is utilized, the change in emissions from the radiation directed into the sensor at the two wavelengths is also small between the two wavelengths. A straight ratio of two close wavelength emissions would typically be effectively equal to one, and no relevant information would be provided by the ratio. Thus, one typically cannot achieve any useful result using a straight ratio of the intensities of the emissions directed outwardly of the chemical sensor from two wavelengths. The prior art use of ratios does not eliminate variation in the sensors or equipment having an effect on the detected emissions.

SUMMARY OF THE INVENTION

Applicant has found that the use of two closely-spaced wavelengths for directing radiation sources into a chemical sensor can result in an absolute reading for the intensity of the emissions $I_1$, and $I_2$ resulting from those directed radiations. Such readings are put into a formula for a value S, wherein the formula eliminates any variations in the readings due to variations in the chemical sensor, or in associated equipment. Thus, an absolute reading from the chemical sensor is provided which can be utilized to make a determination of whether a particular sample vial is evidencing bacterial growth.

To calculate the quantity S the following formula is used:

$$S = 2 \frac{I_1 - I_2}{I_1 + I_2}$$

The value of S is then monitored with time. As will be shown below the value of S does not vary with changing sensor or station-to-station variations. Thus, an absolute reading of S at any time provides an indication of whether the particular sample vial has turned positive at that time. Should a particular "late" sample vial already be positive when received, a technician would be able to determine this fact from an initial reading and calculation of S.

The main inventive feature of this invention is the discovery of this calculation for the ratio quantity S. This quantity provides an absolute indication of whether the particular sample vial is a positive or a negative. Applicant will show this by mathematical proofs, which follow. However, perhaps as importantly, experimental results which are also included in this application show that, in fact, a reliable indication of the sample vial status is reached by calculations of the ratio quantity S.

With prior art systems, wherein the absolute value of any emission reading changes with station-to-station variations or sensor-to-sensor variations, one cannot make a determination based on any reading that a particular vial is a positive. With the inventive system, should a particular vial have already turned positive, one may be able to determine so from an initial reading. If the initial reading indicates the vial is negative, the vial will be tested over time, as in the prior art, to monitor for changes in the S values which indicate a positive sample. With the prior an systems a danger may arise since one is looking for a change in the emissions. If the sample vial has already turned positive, there may be no change in the emission, and thus the vial may never be identified as being positive.

It will now be shown that the quantity S eliminates any variations and provides an absolute reading. In addition to the following mathematical explanation, it should be noted that the experimental evidence disclosed below will show that a reliable absolute value is being calculated. In order to explain the inventive feature of this invention, we assume a sensor matrix with an absorptive sensor material having a wavelength-dependent and pH-dependent transmission $T(\lambda, pH)$, and with an added fluorophore of absorption $R(\lambda)$. A given optical power $p(\lambda)$ at wavelength $\lambda$ directed into the chemical sensor generates an emission intensity photocurrent $I(\lambda, pH)$ in a photodetector of responsivity r and with an emission filter of transmission $T_E$ in front of the active area which is given by the following equation:

$$I(\lambda, pH) = P(\lambda)T_F(\lambda)T_A(\lambda, pH)R(\lambda)T_E r\, g.$$

In this equation, $T_F(\lambda)$ is the transmission of a spectral filter between the source and the sensor. The quantity g is a constant factor which relates to the particular geometrical shape and condition of the chemical sensor. Thus, g will not vary for varying wavelengths. Emissions are read from radiation directed into the sensor at two wavelengths $\lambda_1$ and $\lambda_2$. For a fixed difference between $\lambda_1$ and $\lambda_2$, the difference of the emissions $I_1$ and $I_2$ from the two wavelengths are proportional to the first derivative of the emission from the chemical sensor. The first derivative is closely related to the chemical parameter to be measured; i.e., to the pH-value in this case.

The two emissions may be defined by the equations:

$$I_1 = P(\lambda_1)T_F(\lambda_1)T_A(\lambda_1)R(\lambda_1)T_E r\, g.$$

and $$I_2 = P(\lambda_2)T_F(\lambda_2)T_A(\lambda_2)R(\lambda_2)T_E r\, g.$$

Substituting these equations into the equation for S yields:

$$S = 2\frac{T_1R_1 - T_2R_2}{T_1R_1 + T_2R_2}$$

In this equation, the $P(\lambda)$ quantities have assumed to be constant between $\lambda_1$ and $\lambda_2$. If the two wavelengths are selected to be close, this is a valid assumption. Further, the $T_F(\lambda)$ quantities can also be assumed to be effectively equal if the two wavelengths are kept quite close. Thus, these quantities have been cancelled out in the equation. Further, the $T_A(\lambda)$ quantities have been shortened to simply $T_1$ and $T_2$, and the $R(\lambda)$ quantities have been shortened to simply $R_1$ and $R_2$.

The above equation for S shows also that station-to-station variations and long-time changes in the light source power $P(\lambda)$ have no impact on the calculated S value. In other words, all these artifacts are canceled out. The same cancellation takes place with regard to small changes in the position of the sensor (factor g), aging effects within the photodetector (factor r), and with regard to station-to-station differences in the emission filter transmission (factor $T_E$).

The derivative of S due to changes in T or R, can be shown to be:

$$dS = \left(\frac{dS}{dT_1}\right)dT_1 + \left(\frac{dS}{dT_2}\right)dT_2 + \left(\frac{dS}{dR_1}\right)dR_1 + \left(\frac{dS}{dR_2}\right)dR_2$$

The first and the second term in this equation, or the dT terms, describe variations in the calculated quantity S due to changes in the pH-dependent absorber of the sensor. The third and the fourth term in the equation, or the dR terms, relate to variations in the fluorophore. It can be shown that the first and the second terms cancel out each other, and that the third and the fourth terms cancel out each other, when the difference in the wavelengths $\lambda_1$ and $\lambda_2$ is kept small. We will first look at the dT terms.

The quantity T is related to the absorbance A by the equation:

$$T_A(\lambda, pH) = 10^{-A(\lambda, pH)}$$

Substituting this equation into the two dT terms of the ds equation yields:

$$dS_A = \frac{4\ln 10\, R_1R_2T_1T_2\,[dA_2 - dA_1]}{(T_1R_1 + T_2R_2)^2}$$

This equation is zero where the following condition applies:

$$dA_1 = dA_2.$$

The absorbance A of a sensor can be described by the formula:

$$A(\lambda, pH) = a(\lambda, pH)c\, h,$$

wherein a is the wavelength and pH-dependent absorption coefficient of the sensor material, c is the concentration of the absorptive material, and h is its effective thickness. Production related variations in the sensor absorbance A can result from variations in c and/or variations in h. Thus, the change in A for both changes in c and h is taken as follows:

$$dA = \left(\frac{dA}{dc}\right)dc + \left(\frac{dA}{dh}\right)dh.$$

Substituting the last two equations yields:

$$dA = a(\lambda)[h\, dc + c\, dh].$$

Thus, potential variation of the above equation due to dc and/or dh is shown to be proportional to $a(\lambda)$. If the difference in the two wavelengths is kept small then there will be little change in $a(\lambda)$. With regard to the h, dc, c, and dh quantities, they will be constant for any single given sensor. Though these quantities vary between sensors, they are constant for any particular sensor. Thus, since the two wavelengths are directed into a single sensor with a single test system, it can be assumed that those quantities will all be equal for both of the wavelengths tested. Since it can also be assumed that the $a(\lambda)$ quantity is equal for the two wavelengths, it can be assumed that the dA quantities will be equal for the two wavelengths. One can make this assumption, since the two wavelengths are kept very close. Thus, it can be assumed that the two dA terms are equal and, consequently, the two dT terms cancel out each other.

In many potential chemical sensor materials, isobestic points show a maximum change of the first derivative with changing chemical parameter to be measured. Therefore, applicant preferably selects the two wavelengths $\lambda_1$ and $\lambda_2$ to be closely spaced to an isobestic point. Now we will look at the dR terms in the equation for dS. If we follow the same steps as in calculating the dT terms, and taking into account that the fluorophore's absorption R is related to the fluorophore's transmission T by the simple equation:

$$T = 1-R,$$

then we obtain for the variation in S due to production-related variations within the fluorophore, $$dS_F = \frac{4\ln 10\, T_1 T_2 [(1-R_1) dA_{F1} - (1-R_2) dA_{F2}]}{(T_1 R_1 + T_2 R_2)^2}$$

This variation can be eliminated under the condition.

$$(1-R_1) dA_{F1} = (1-R_2) dA_{F2}.$$

This condition can also be best approximated where the difference in wavelength between $\lambda_1$ and $\lambda_2$ is kept very small.

Thus, by calculating the quantity S, and by keeping the two wavelengths relatively close, one is able to cancel out variations in the emissions due to lot-to-lot variations in the sensor absorber or the fluorophore and also station-to-station variations in the equipment. In this way, one is able to achieve an absolute reading of whether a particular sample vial is a positive or a negative. As stated above, it is important that the reading be taken using wavelengths selected at a location on the emissions curve of the sensor material wherein the first derivative of that curve shows maximum change with changing chemical parameter to be measured. This will be explained in more detail below.

Applicant has determined that it is preferable that the two wavelengths be spaced by an amount less than 100 nm. Further, it is preferred that the two wavelengths be spaced by an amount that is greater than 10 nm. If a smaller wavelength difference is selected, the noise that is a reality in all electronic components used to measure the emissions and to calculate the quantity S would begin to interfere with the small changes in the emission intensities between the two wavelengths. Thus, although in an idealized situation the wavelengths would be as close as possible, due to realities in the electronic components it is preferred that a difference of at least 10 nm be maintained. In a most preferred embodiment the wavelengths are spaced by approximately 20 nm.

As to the particular area where the wavelengths are selected, it is preferred that the wavelengths be selected to be near an isobestic point for the material. An isobestic point of a material is a point where independent of the value of the chemical parameter to be measured, the sensor will have a relatively fixed emission intensity, but show maximum change in the first derivative. The isobestic points of a sensor material can be best determined experimentally by varying the chemical parameter to be measured, and running several tests to develop curves as will be discussed below. These curves will point to the isobestic point.

In a most preferred embodiment, Applicant chooses points equally spaced above and below an isobestic point. However, it should be understood that the two points could be slightly above the isobestic point or both slightly below the isobestic point.

In a second method according to the present invention, the emissions resulting from two distinct wavelength radiation sources directed into the chemical sensor are monitored. The intensity of one of the two sources is modified until the two emission intensities are equal. The intensity of the two radiation sources are then measured, and a ratio found from the formula:

$$S^* = 2 \frac{P_2 - P_1}{(P_2 + P_1)}$$

This ratio will provide an absolute reading of whether a particular sample vial is a positive, evidencing bacterial growth. It can be shown from the above intensities equations that when the two emission intensities are equal, the following condition exists:

$$P_1\, T_1\, R_1 = P_2\, T_2\, R_2$$

It can also be shown that the method using the second formula for $S^*$, is equal to the method using the first formula for S. Again, both of these methods provide an indication of whether a particular sample vial is evidencing bacterial growth, without any interference due to variations in the makeup of the chemical sensor, or in station-to-station variations resulting from the equipment utilized to direct radiation into the sensor, and to read emissions emerging from the sensor.

As described, the inventive formula has been shown to eliminate the variations which are expected from station-to-station changes in the apparatus associated with the sensor, or in variations with regard to the sensor itself. Several systems for accomplishing the inventive method are disclosed below.

These and other features of the present invention can be best understood from the following specification and drawings, of which the following is a brief description.

DETAILED DESCRIPTION OF THE PREFERRED EMBODIMENT

Figure 1:
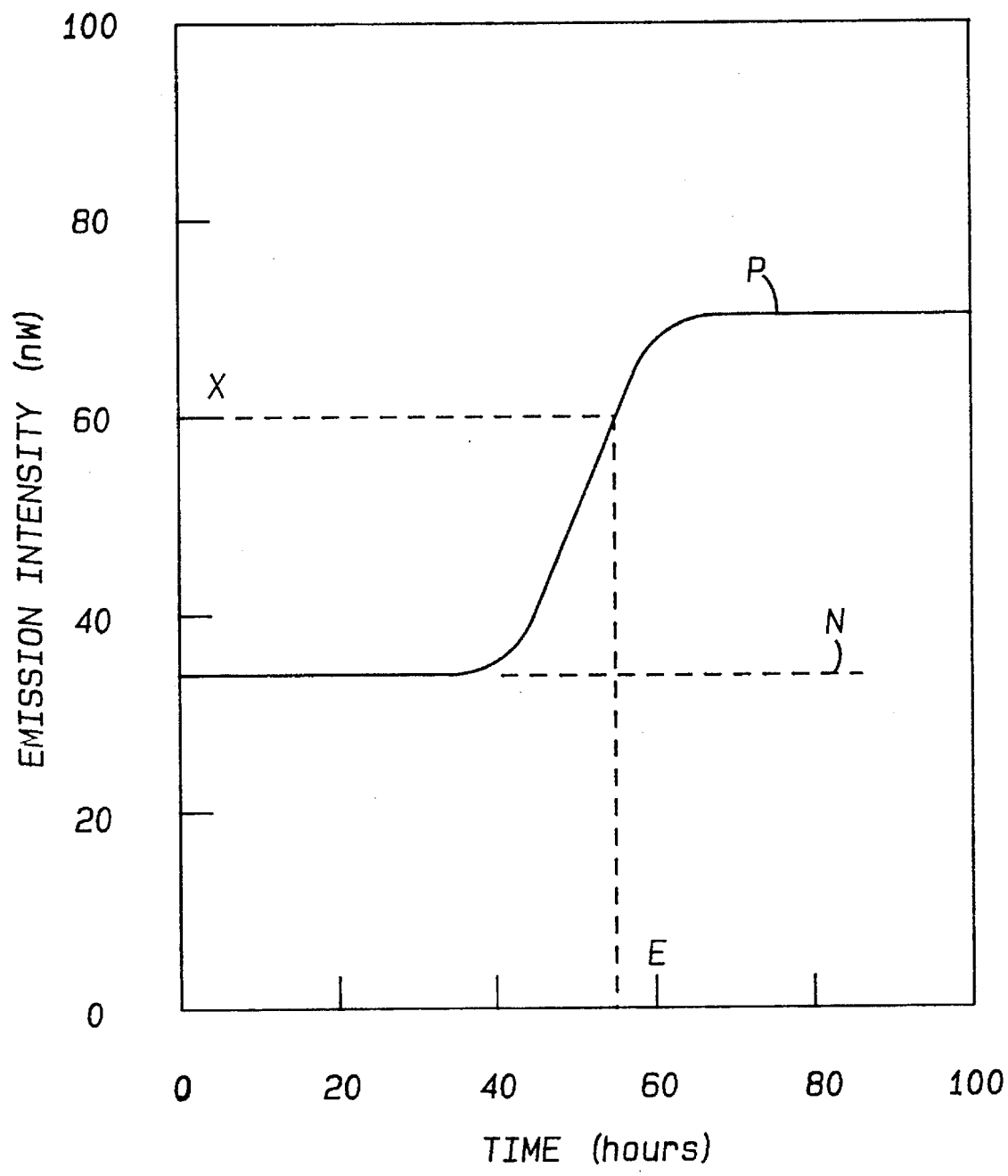
FIG. 1 is a highly schematic view of a typical curve for emissions from a chemical sensor over time.

FIG. 1 illustrates the basic detection logic which is utilized with known chemical sensors based on intensity readings. The emission intensities are monitored, stored and plotted against time for each sample vial. A change in the emission intensity value such as is shown at time E for line p would indicate that that particular sample vial is a "positive" and is undergoing bacterial growth. The relatively straight line N, which does not change its emission intensity would be typical of the expected readings for a negative sample vial.

Problems arise with the prior art systems, however, since the value X associated with the intensity from the line P at the time it has evidenced bacterial growth can vary. That is, a second vial which is also a positive, may have all of its emission values being below all of the values read for the negative sample vial shown by line N. This could include both those before and after the time E where the second vial begins to evidence bacterial growth. Thus, one cannot look at any given point on the emission reading for a particular sample vial and make a determination of whether the sample vial is a positive. Rather, one must monitor each sample vial over a period of time and look for changes in the emissions. Problems arise when sample vials are delivered to a test site after an undue length of time. Such a sample vial may arrive at the test site having already gone past the point E where it is experiencing bacterial growth. After that change, there may be little additional change in the emission readings. One would thus have difficulty predicting that such a sample is a positive, based solely on monitored changes.

Since the absolute value of the reading provides little information, it is difficult to make any determination relative to that vial.

The present invention allows one to identify so-called "late" sample vials, by making a reading that provides an absolute number which can be looked at any given point to make a prediction of whether the particular sample vial is positive or still negative at that time.

Applicant has solved the above-discussed problems by calculating a quantity that includes a ratio of the differences of the monitored intensities and the sums of the monitored intensities. Preferably, the monitored intensities are measured by directing two radiation sources at different wavelengths into the chemical sensor and measuring the emerging emission intensities. The wavelengths are spaced by a small margin, and are selected to be in an area wherein the emission spectrum between the two wavelengths shows maximum change with changing chemical parameter to be measured. Due to the pronounced change in the area of the two wavelengths, sufficient differences will exist between the two emissions such that an indication of the state of the culture in the sample vial will be provided by the emissions.

The quantity S which is to be measured, can be shown to have eliminated any interference due to station-to-station variations or sensor-to-sensor variations by the calculations which follow. In addition, the experimental evidence provided by FIG. 3 makes it clear that the inventive method does work.

The ratio S is calculated as follows:

$$S = 2 \frac{I_1 - I_2}{(I_1 + I_2)},\quad (1)$$

where $I_1$ and $I_2$ are the emission photocurrents measured at the wavelengths $\lambda_1$ and $\lambda_2$.

A main feature of this invention is the discovery of this formula which provides an absolute reading and eliminates variations. A given wavelength $\lambda$ directed into a chemical sensor having an added fluorophore with an absorption $R(\lambda)$ generates emission intensity photocurrent $I(\lambda, pH)$ in a photodetector of responsivity r and with an emission filter of transmission $T_E$ in front of the active area which is given by the following equation:

$$I(\lambda, pH) = P(\lambda) T_F(\lambda) T_A(\lambda, pH) R(\lambda) T_E r\, g. \quad (2)$$

In equation (2), g is a constant factor which relates to the particular geometrical shape and condition of the chemical sensor. Emissions are read from radiation directed into the sensor at wavelengths $\lambda_1$ and $\lambda_2$.

From equation (2) the two emissions are defined by the equations:

$$I_1 = P(\lambda_1) T_F(\lambda_1) T_A(\lambda_1) R(\lambda_1) T_E r\, g. \quad (3)$$

and $$I_2 = P(\lambda_2) T_F(\lambda_2) T_A(\lambda_2) R(\lambda_2) T_E r\, g. \quad (4)$$

Substituting equations (3) and (4) into equation 1 yields:

$$S = 2 \frac{T_1 R_1 - T_2 R_2}{T_1 R_1 + T_2 R_2} \quad (5)$$

In equation (5), the $P(\lambda)$ quantities have assumed to be constant between $\lambda_1$ and $\lambda_2$. If the two wavelengths are selected to be close, this is a valid assumption. Further, the $T_F(\lambda)$ quantities can also be assumed to be effectively equal if the two wavelengths are kept quite close. Thus, these quantities have been cancelled out in equation (5). Further, the $T_A(\lambda)$ quantities have been shortened to simply $T_1$ and $T_2$. Also, the $R(\lambda)$ quantities have been shortened to simply $R_1$ and $R_2$.

The derivative of S due to changes in T or R, can be shown to be:

$$dS = \left(\frac{dS}{dT_1}\right) dT_1 + \left(\frac{dS}{dT_2}\right) dT_2 + \left(\frac{dS}{dR_1}\right) dR_1 + \left(\frac{dS}{dR_2}\right) dR_2 \quad (6)$$

The two dT terms are variations in sensor emissions due to the pH-dependent absorber of the sensor, and variations therein. The two dR terms relate to variations due to the fluorophore. The two dT quantities and the two dR quantities can be shown to be cancelled out under certain conditions. We will first look at the two dT quantities. It can be shown that the quantity T is related to the absorbance A by the equation:

$$T_A(\lambda, pH) = 10^{-A(\lambda, pH)} \quad (7)$$

Substituting equation (7) into the two dT components of equation (6) yields for the two dT components:

$$dS_A = \frac{4 \ln 10\, R_1 R_2 T_1 T_2\, [dA_2 - dA_1]}{(T_1 R_1 + T_2 R_2)^2} \quad (8)$$

Equation (8) is zero where the following condition applies:

$$dA_1 = dA_2. \quad (9)$$

The absorbance A of a sensor can be described by the formula:

$$A(\lambda, pH) = a(\lambda, pH) c\, h, \quad (10)$$

Wherein a is the wavelength and pH-dependent absorption coefficient of the sensor material, c is the concentration of the material, and h is its effective thickness. Production related variations in the sensor absorbance A can result from variations in c or h. Thus, we will take the derivative of the equation for both changes in c and h, as shown:

$$dA = \left(\frac{dA}{dc}\right) dc + \left(\frac{dA}{dh}\right) dh. \quad (11)$$

Substituting equation (10) into equation (11) yields:

$$dA = a(\lambda)[h\, dc + c\, dh]. \quad (12)$$

Thus, potential variation by the dT components of equation (6) is shown to be proportional to $a(\lambda)$. If the difference in the two utilized wavelengths is kept small then there will be little change in $a(\lambda)$. As described above, the h, dc, c, and dh quantities will all be equal for the two wavelengths directed into the single sensor. One can thus assume that the two dT terms of equation (6) are cancelling each other out.

Again, preferably, the two wavelengths are selected to be closely spaced in an area wherein the first derivative of the emission curve with changing chemical parameter is pronounced. In this way, even though the difference in wavelengths is small, the difference in the emissions between the two wavelengths will be more pronounced. This coupled with the inventive calculation of the quantity S will provide an absolute indication of whether the particular sample vial is a positive or a negative at that time.

Now we will look at the dR terms in the equation for dS. If we follow the same steps as in calculating the dT terms, and taking into account that the fluorophore's absorption R is related to the fluorophore's transmission T by the simple equation:

$$T=1-R, \qquad (13)$$

then we obtain the variation in S due to the production-related variations within the fluorophore.

$$dS_F = \frac{4\ln10\, T_1 T_2\, [(1-R_1)dA_{F1} - (1-R_2)dA_{F2}]}{(T_1 R_1 + T_2 R_2)^2} \qquad (14)$$

This variation can be eliminated under the condition.

$$(1-R_1)dA_{F1}=(1-R_2)dA_{F2}. \qquad (15)$$

For this condition to be met, then $R_1$ must equal $R_2$ and $dA_{F1}$ must equal $dA_{F2}$. These conditions can be best approximated where the difference in wavelength between $\lambda_1$ and $\lambda_2$ is kept very small.

Figure 2:
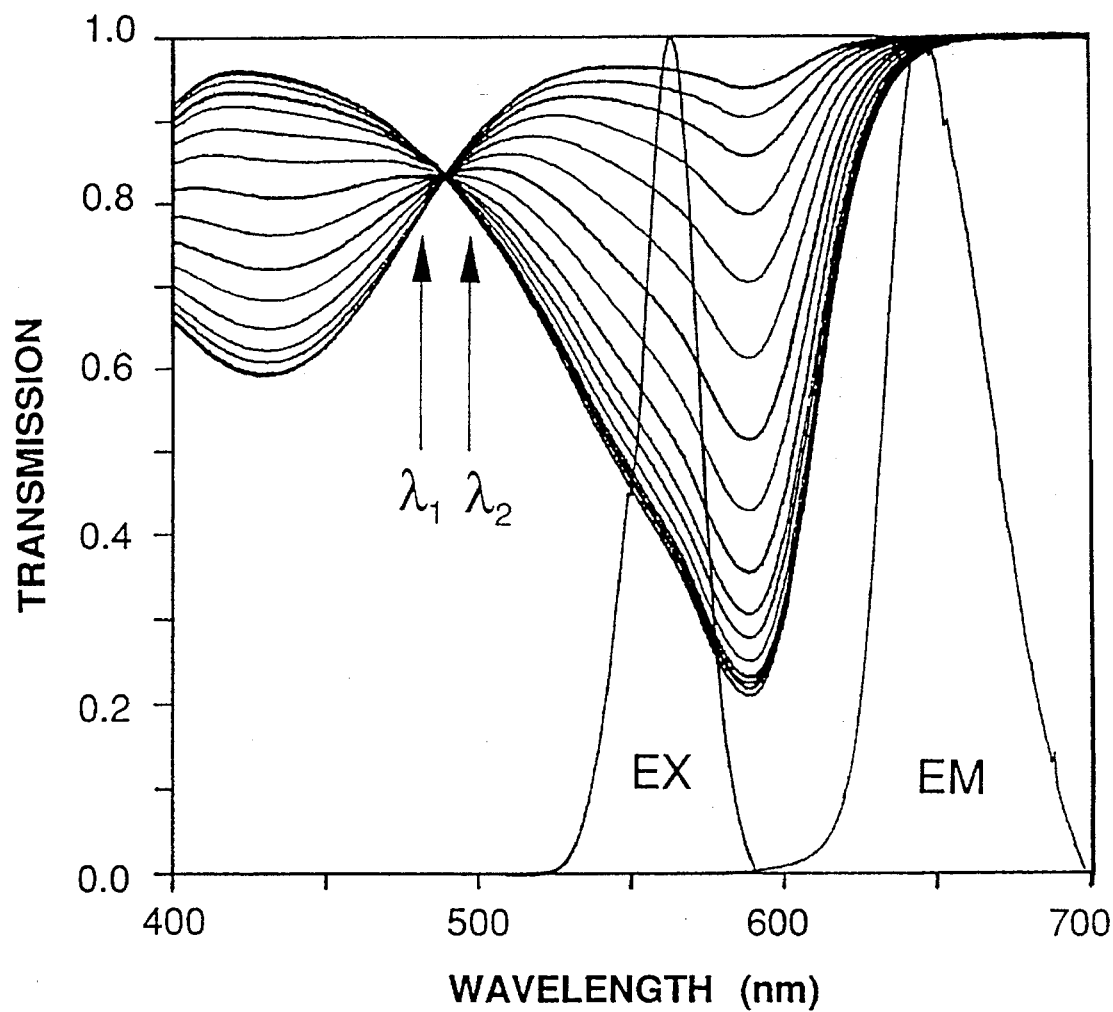
FIG. 2 is a plot of several curves showing the absorber transmission versus wavelength for varying chemical parameter to be measured.

FIG. 2 is a plot for the absorber transmission plotted against a varying wavelength of radiation being directed into the sensor. The several curves shown in this figure, represent various sample vials, which vary due to variations in the chemical parameter to be measured; i.e., the pH value.

To develop the curves such as shown in FIG. 2, one takes a single type of sensor and varies the concentration of the quantity that the type of sensor tests with varying wavelength. Each curve shown in FIG. 2 represents a distinct sample vial, or varying conditions within a single vial. The wavelength is changed, and the emission intensity is read for each vial or sensor condition. As one example, several sample vials each including an identical sensor may be tested with different pH concentration for a sensor which responds to changes in pH concentration. A curve is plotted for each vial, and the graph of FIG. 2 is then achieved. The point where all of the curves cross is the isobestic point. As an alternative to this method, a single sample vial may be connected to a source of a material which will change the pH concentration. The pH concentration would then be incrementally adjusted, and the curves generated for each incremental concentration.

A major problem that the instant invention addresses is that the sensor material will vary with the manufacturing lots. Thus, a type of sensor prepared at a first period of time may have distinct characteristics than a type of sensor which is to be identical to the first type of sensor, but which is prepared some time in the future.

Note that the general shape of the curves can be said to be similar to a butterfly with two opposed wings and a center. The center point is the isobestic point for the particular type of sensor. With variations in the sensor or in station-to-station variations, this "butterfly" shape could move upwardly or downwardly. Thus, a second sample vial having a second production lot in sensor material could have a curve quite similar to a first sample vial, only downshifted by 0.2 on its emissions from all of the readings for the first sensor. Due to this fact, the prior art systems which utilize readings of the emissions have been unable to make any determination based on any single reading.

Note that in the prior art, the areas EX and EM are often utilized with chemical sensors to make the readings. Note also that the isobestic point is at an area of relatively high change in the slope of the curves, and spaced from the EX and EM areas.

Figure 3:
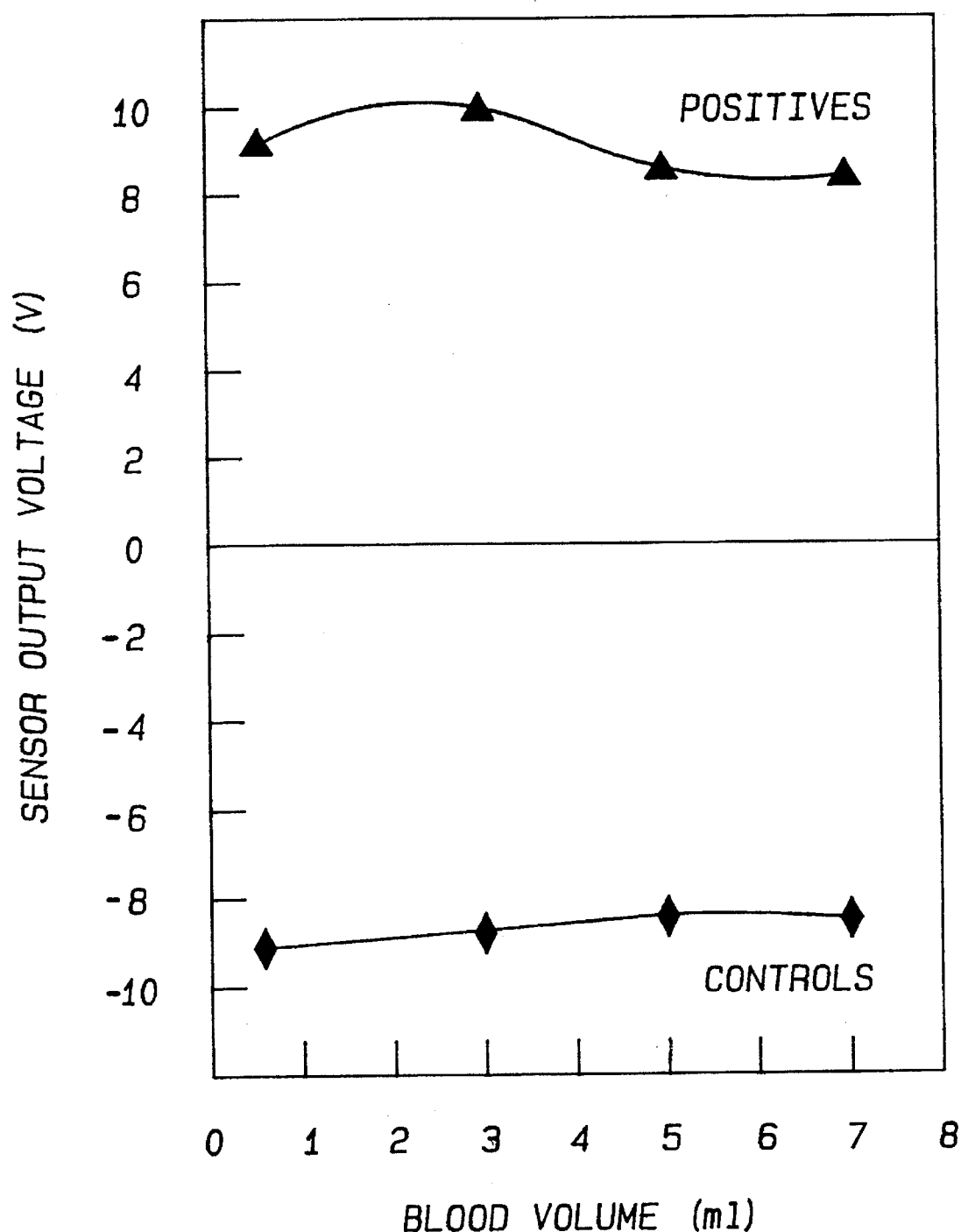
FIG. 3 shows S readings for the inventive method.

FIG. 3 shows the results of samples tested using the inventive method described above. The emissions are not only relatively predictable and constant for the positives and for the negative controls, they also change their sign between positive and negative. Thus, with the inventive method, a first reading will provide a very good indication of whether the particular sample is already positive. The results illustrated in FIG. 3 were achieved by four tests-on four vials that were known to be positive, and four control vials. As shown, although the wavelengths utilized were spaced by a distance of only 20 nm, a clear differentiation between positive and negative vials is achieved, and further an absolute prediction can be made from the measured emission intensities.

In addition, since the sign changes, it may be possible to rely on only the difference calculation as opposed to calculating the ratio. This variation may not be as valid if the wavelengths are selected to be removed from the isobestic. As the wavelengths move away from the isobestic point, it is expected that the sign of the calculated values may no longer change between positives and controls.

In a further feature of this invention, one can calculate a quantity S using a second logic. In the second logic, two radiation sources spaced by a small wavelength difference are directed into the sample vial. The emerging emission intensities are again measured and compared. If the emerging emission intensities are unequal, then the intensity of one of the radiation sources being directed into the vial is modified. This modification is continued until the emission intensities are equal. At that point, the intensities of the two radiation sources being directed into the sample vial are measured.

Since at that point it is known that the I quantities calculated in equations (3) and (4) would be equal for these two wavelengths, equations (3) and (4) (and the other assumptions used in the above calculations) yield the equation;

$$P_1\, T_1\, R_1 = P_2\, T_2\, R_2 \qquad (16)$$

for this particular situation. $p_1$ and $p_2$ are the measured adjusted intensities. The quantities T and R have the same meanings as before. If we then calculate the quantity S* as being equal to:

$$S^* = 2\frac{P_2 - P_1}{(P_2 + P_1)} \qquad (17)$$

we arrive at a value for S* that is equivalent to the earlier S value, and should be as useful in determining whether the particular sample vial is negative or positive.

By using equations (16) and (17), it can be shown that the calculation for S* in equation (17) is the same as the calculation for S in equation (5) as follows:

$$S^* = 2\frac{T_1 R_2 - T_2 R_1}{T_1 R_1 + T_2 R_2} \qquad (18)$$

Thus, this second test logic is similar to the first. Again, it is preferred that the wavelengths are kept very close, and centered about or in the vicinity of an area wherein the first derivative of the slope is changing. The preferred area is the area around the isobestic point.

Applicant will now disclose several systems for achieving the inventive goals.

Figure 4:
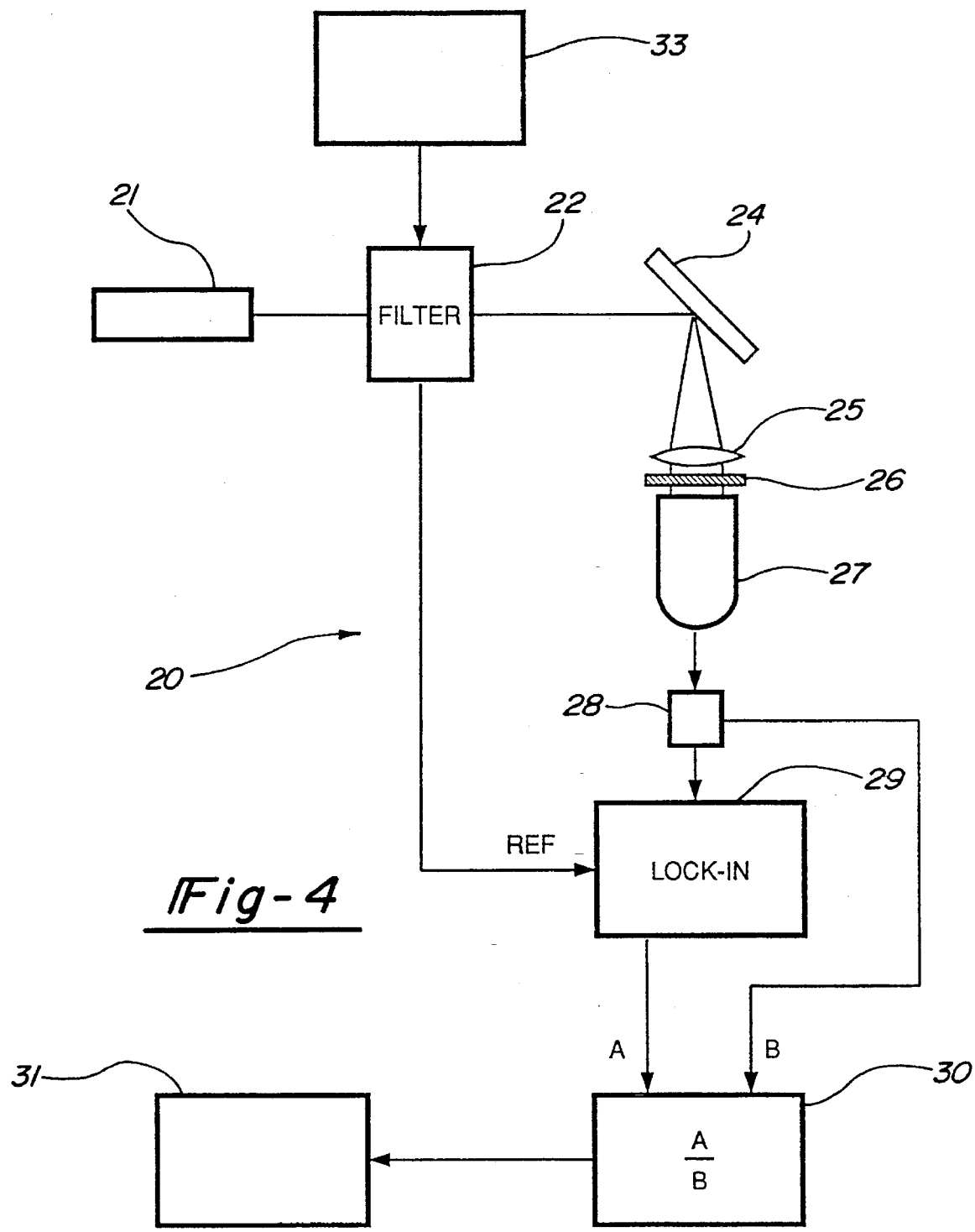
FIG. 4 is a schematic view of a system for accomplishing the present invention.

A system 20 as shown in FIG. 4 includes a light source 21 which directs a beam of radiation through a wavelength-tunable narrow-band filter 22 and into sensor material 24. The center wavelength of the narrow-band filter is located at some point between two desired wavelengths. Preferably, the center wavelength would be located at the isobestic point for the sensor material. Acousto-optic, electro-optic, piezoelectric or other tunable filters are suitable devices. Radiation emerging from sensor material 24 is directed to an optical lens system 25, emission filter 26 and a photodetector 27.

For sensor configurations with a high intensity of re-emerging light, simple photodiodes can be used for the photodetector. For fluorescent sensors high-sensitivity photodetectors such as photomultipliers may be required. The signal output of photodetector 27 is fed to a DC/AC splitter 28. The AC output of splitter 28 is connected to the signal input of a lock-in amplifier 29. The AC output is equivalent to the difference term in calculating S. The output of lock-in amplifier 29 is fed to one input of a ratio unit 30. The other input of the ratio unit 30 is connected with the DC output of the splitter 28. The DC output is equivalent to one-half the sum in calculating S. Thus, ratio unit 30 is provided with the necessary measured quantities to calculate S. The output of the ratio unit 30 is fed to a data acquisition unit 31. The embodiment also includes a driver 33, which is connected to the wavelength tunable filter 22. Filter 22 has a trigger output connected with the reference input of the lock-in amplifier 29. In this and all other embodiments, a computer could replace the ratio unit and data acquisition unit.

Since lock-in amplifier 29 is synchronized with filter scanning, the lock-in amplifier output signal is proportional to the difference of the photocurrents $I_1$ and $I_2$ obtained at the limiting wavelengths for the tunable filter. For a fixed scanning lift this difference will be proportional to the first derivative of the sensor material transmission at the center point.

The signal at the DC output of splitter 28 is proportional to the average light intensity obtained from the sensor material at the center point between the two wavelengths which are being utilized here and preferably the isobestic point. The average photocurrent is one-half $I_{1+I2}$.

In the ratio unit 30 the first derivative of the sensor material transmission is normalized to the average light intensity obtained for illumination of the sensor material at the isobestic point.

The ratio unit 30 calculates the quantity S by the equations described above.

Figure 5:
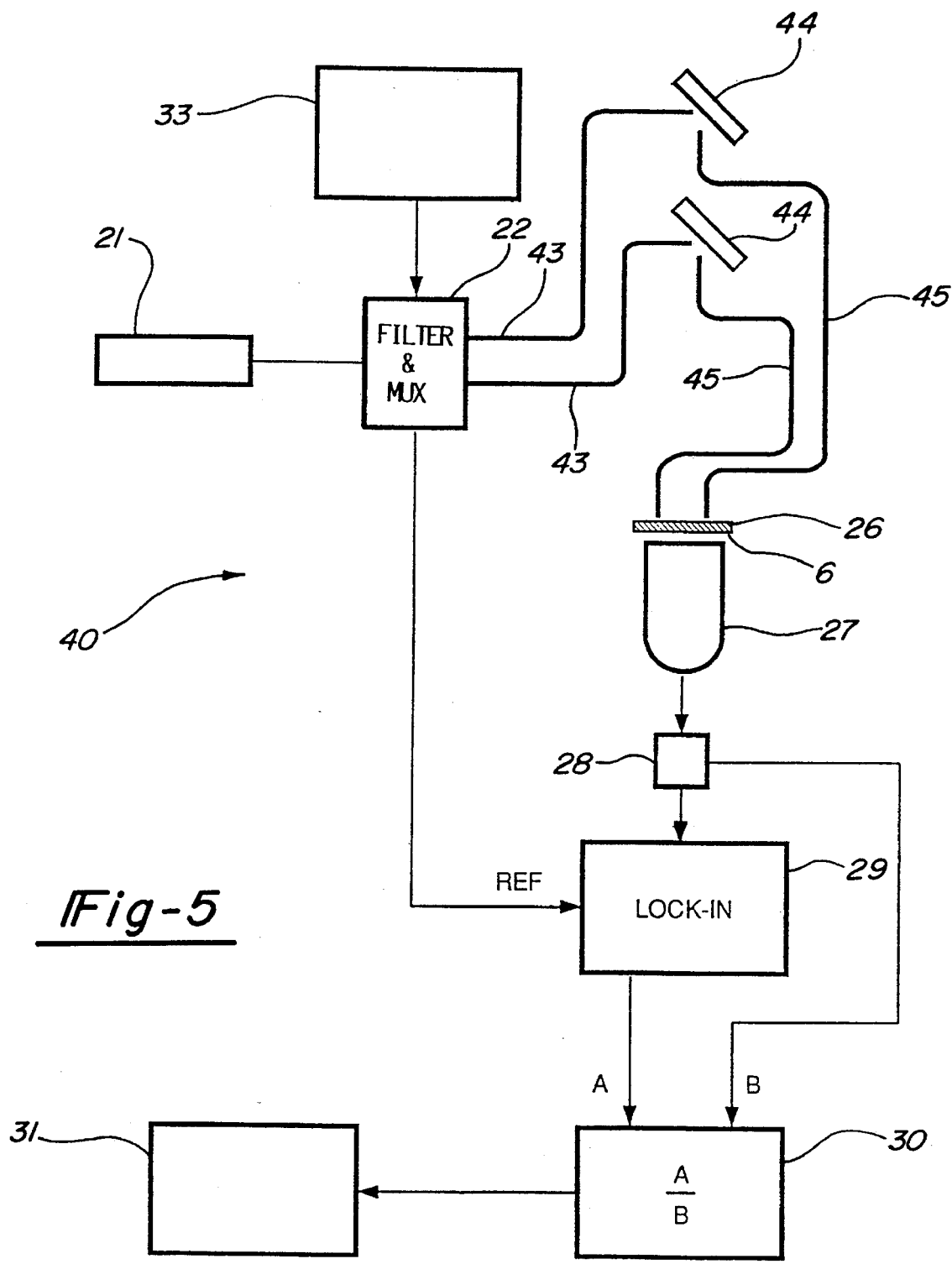
FIG. 5 is a schematic of a second system for accomplishing the inventive method.

FIG. 5 shows chemical sensor arrangement 40 which includes a plurality of sensors 44 associated with several sample vials. Radiation is directed into each sensor 44 by fibers 43, and the emissions from the sensors are directed out of the vials by fibers 45. In this embodiment, a single light source 21, a single tumble filter 22, emission filter 26 and photodetector 27 can be utilized to excite and monitor a large number of sensors and sample vials.

In FIG. 5, the wavelength-tunable filter 22 is combined with an optical multiplexer that directs excitation radiation serially towards the plurality of the chemical sensors via the fibers 43.

Figure 6:
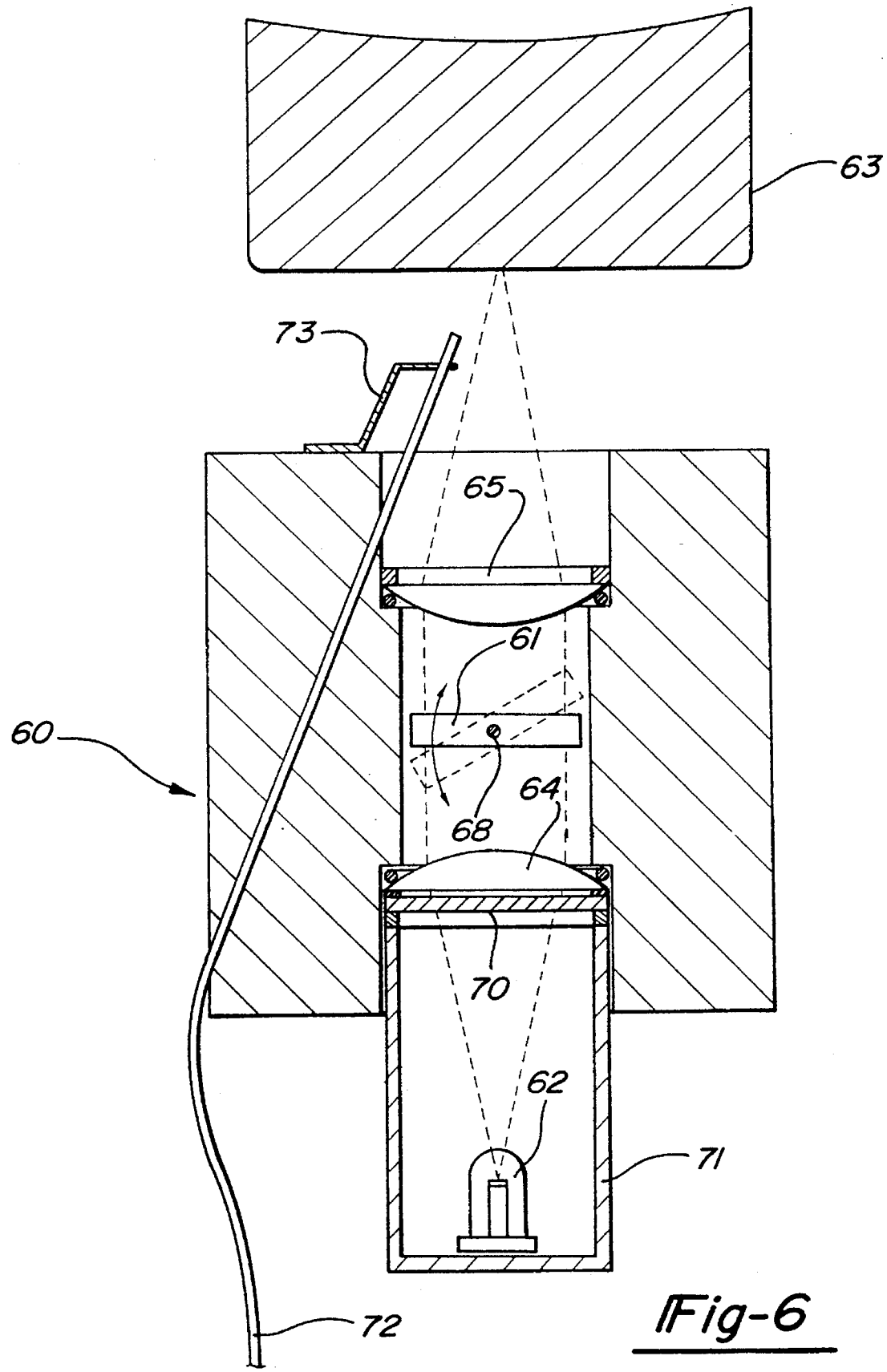
FIG. 6 is a schematic of a third system for accomplishing the inventive method.

FIG. 6 shows a system 60 with a periodically tilted filter 61 that is used as the wavelength-tunable filter. In this system, the beam-of the radiation source 62 is focused onto the sensor material 63 by two condenser lenses 64 and 65. The tilting narrow-band interference filter 61 is inserted into the radiation beam between lenses 64 and 65. Filter 61 is periodically tilted around a pivot point 68. For normal incidence, the center wavelength of the interference filter is located just above an isobestic point of the sensor material. For the sensor material shown in FIG. 2, the isobestic point is located at 490 nm. If this were the material utilized in the FIG. 6 system, the center wavelength of filter 61 for normal incidence might be set to 500 nm. By tilting the filter periodically at an angle of, for example, 30°, the center wavelength will shift periodically between a $\lambda_2=500$ nm to $\lambda_1=480$ nm. Thus, the chemical sensor will be excited by radiation sources just above and just below the isobestic point. The embodiment shown in FIG. 6 also contains an additional filter 70 which blocks a long-wavelength light component of source 62 that may pass filter 61. The light source 62 is mounted inside a lamp housing 71. Light re-emerging from sensor 63 is collected by a fiber 72, having one end held in a clamp 73.

The foregoing sample systems are particularly well suited for calculating the quantity S which utilizes the intensities of the emissions. The system shown in FIG. 7, on the other hand, is particularly well suited for the calculation of the quantity S* which utilizes the intensity of the radiation sources being directed into the system.

Figure 7:
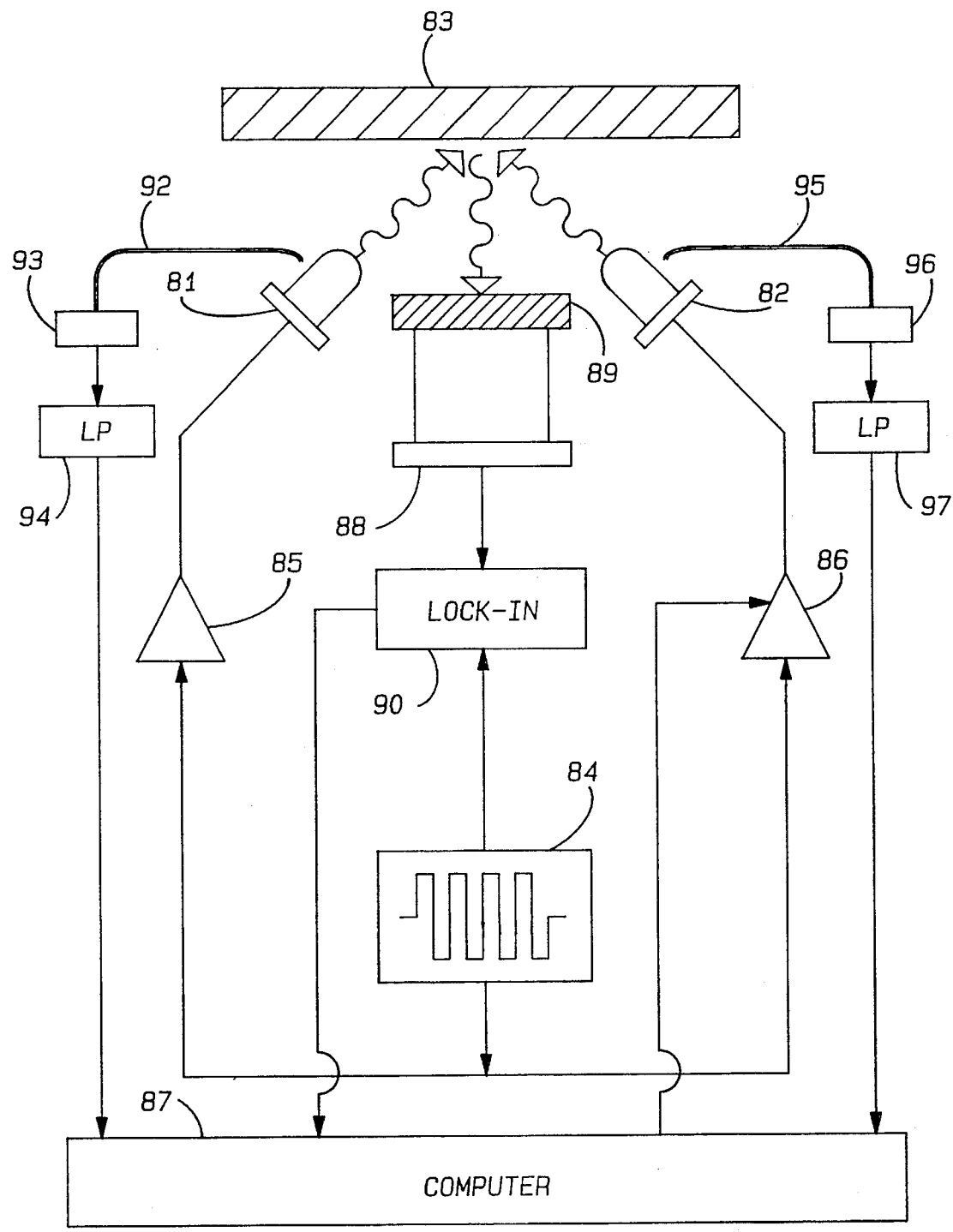
FIG. 7 is a schematic of a fourth system for accomplishing the inventive method.

In FIG. 7, two distinct light sources 81 and 82 are directed to the chemical sensor 83. Preferably, two LEDs of different emission center wavelengths are utilized. First radiation source 81 and second radiation source 82 are operated in an alternating mode by means of a square-wave signal generator 84. The signal output of generator 84 is connected by a first amplifier 85 to light source 81, and by a second amplifier 86 to light source 82. The gain of amplifier 86 is controlled by a computer 87. The light re-emerging from the sensor material 83 is measured by photodetector 88. If the sensor material 83 contains a fluorophore, an emission filter 89 is positioned between sensor material 83 and photodetector 88. The output of the photodetector 88 is fed to the signal input of a lock-in amplifier 90 having a reference input connected to the trigger output of-square wave generator 84. The signal output of the lock-in amplifier is fed to the computer 87.

part of the light emitted by light source 81 is collected by means of a first optical fiber 92 and directed to a first photodiode 93. The output of photodiode 93 is connected to the computer 87 via a low-pass filter 94. Similarly, part of the light emitted by second light source 82 is collected by a second optical fiber 95 and directed to photodiode 96, and then connected to computer 87 via a low-pass filter 97. Thus, fibers are disposed to take a portion of the radiation directed from sources 81 and 82 and direct the measured intensity values to a computer. In this way, one is able to monitor the intensity of the radiation sources. Further, the computer 87 controls the intensity of the second radiation source 82 and allows it to be varied as described above, such that the quantity S* can be calculated using the above calculations and logics.

Although particular systems have been disclosed for achieving the inventive method, it should be fully understood that many types of circuitry for calculating the above-described quantities may be utilized. Further, although a light source is preferably utilized in this application, it should be understood that other radiation sources may be able to achieve the inventive goals.

It should also be understood that the present invention could apply to sensors that only contain a fluorophore, but no absorber, or to sensors that only contain an absorber, but no fluorophore. Most chemical sensor materials currently in use are prepared from combinations of fluorophore and absorber materials, and thus a wide spectrum of chemical sensor materials will be found in the field. preferred embodiments of this invention have been disclosed. It should be understood, however, that certain modifications would come within the scope of this invention. For that reason, the following claims should be studied in order to determine the true scope and content of this invention.

I claim:

1. An apparatus for testing a sample vial containing a chemical sensor to determine whether the sample vial is evidencing bacterial growth, said apparatus comprising:

light radiation source means capable of directing a first radiation of light and a second radiation of light into a chemical sensor in a sample vial, said first radiation being at a first wavelength above an isobestic point of said chemical sensor and said second radiation being at a second wavelength below said isobestic point;

means for detecting a first intensity of an emission from said chemical sensor due to said first radiation of light and detecting a second intensity of an emission from said chemical sensor due to said second radiation of light;

means for calculating a ratio of (i) the difference between said first and second emission intensities detected by said detector means and (ii) the sum of said first and second emission intensities detected by said detector means; and means for determining whether said sample vial is evidencing bacterial growth based on said calculated ratio.

2. An apparatus as recited in claim 1, wherein said light radiation source means includes a single light source, and a filter capable of directing two distinct wavelength radiations into said chemical sensor.

3. An apparatus as recited in claim 2, wherein a pivoting filter is utilized.

4. An apparatus as recited in claim 2, wherein a scanning filter is utilized.

5. An apparatus as recited in claim 1, wherein said light radiation source means includes a pair of light radiation sources.

6. An apparatus as recited in claim 1, wherein said light radiation source directs each of said two distinct wavelengths at a distinct intensity, a second detector is included to detect said distinct intensities, and said detected values are the intensities of said light radiation sources directed into said sample vial.

7. An apparatus as recited in claim 6, wherein said calculating means compares said detected intensities at said two wavelengths, and the system includes means to vary the intensity directed at one of said wavelengths relative to the intensity of the other wavelength until said detected intensities are equal.

8. An apparatus as recited in claim 1, wherein said detected values are said detected intensities of the emissions from said chemical sensor.

* * * * *